(12) United States Patent
Higashiguchi

(10) Patent No.: US 6,327,021 B1
(45) Date of Patent: Dec. 4, 2001

(54) MASK INSPECTION SYSTEM AND METHOD OF MANUFACTURING SEMICONDUCTOR DEVICE

(75) Inventor: Hisayoshi Higashiguchi, Hyogo (JP)

(73) Assignees: Mitsubishi Denki Kabushiki Kaisha, Tokyo; Ryoden Semiconductor System Engineering Corporation, Hyogo, both of (JP)

( * ) Notice: Subject to any disclaimer, the term of this patent is extended or adjusted under 35 U.S.C. 154(b) by 0 days.

(21) Appl. No.: 09/215,925

(22) Filed: Dec. 18, 1998

(30) Foreign Application Priority Data

Jul. 6, 1998 (JP) .................................................. 10-190190

(51) Int. Cl.[7] ........................... G03B 27/52; G03B 27/32; G06K 9/00
(52) U.S. Cl. ................................ 355/30; 355/77; 382/144
(58) Field of Search .................................. 355/75, 76, 77, 355/30, 67; 382/144; 437/225; 73/28.04

(56) References Cited

U.S. PATENT DOCUMENTS 4,801,352 * 1/1989 Piwczyk ................................. 156/345
5,728,602 * 3/1998 Bellows et al. ........................ 437/225
6,038,015 * 3/2000 Kawata .................................... 355/67
6,082,179 * 7/2000 Jeon et al. ............................ 73/28.04

FOREIGN PATENT DOCUMENTS

| 56-150827 | 11/1981 | (JP) . |
| 10-020478 | 1/1998 | (JP) . |

* cited by examiner

Primary Examiner—Russell Adams
Assistant Examiner—Peter B. Kim
(74) Attorney, Agent, or Firm—McDermott, Will & Emery

(57) ABSTRACT

There is described a mask inspection system suitable for reliably removing dust particles from a mask. The system is intended for eliminating the necessity of repetition of dust particle inspection by simultaneous removal of dust particles and checking of the same. When dust particles are detected on a mask, the dust particles are removed. A gas blowing device and a dust particle suction device are disposed in positions where they face the mask. The gas blowing device squirts high-pressure gas to the dust particles from above, and the dust particle suction device sucks the dust particles from blow. A particle counter is connected to the dust particle suction device. When the particle counter counts the number of dust particles, the dust particles are determined to be removed from the mask.

7 Claims, 4 Drawing Sheets

MASK INSPECTION SYSTEM AND METHOD OF MANUFACTURING SEMICONDUCTOR DEVICE

BACKGROUND OF THE INVENTION

1. Field of the Invention

The present invention generally relates to a mask inspection system and a method of manufacturing a semiconductor device, and more particularly, to a mask inspection system suitable for reliably removing dust particles from a mask, as well as to a method of manufacturing a semiconductor device suitable for reliably removing dust particles from the mask prior to an exposure process.

2. Description of the Background Art

In the process of manufacturing a semiconductor device, a wafer is subjected to exposure through use of a mask. Removing dust particles from the wafer prior to the exposure process is important for correct manufacture of a semiconductor device. For instance, a system utilizing scattered light of laser light is known as a system for detecting dust particles existing on the mask. In addition to detecting the presence of dust particles, the foregoing conventional system is capable of acquiring information such as the positions and sizes of dust particles.

Where dust particles are detected during the mask inspection process, the dust particles are usually blown away by air through manual or automated operations. By means of these operations, dust particles can be removed from a mask before a wafer is exposed through use of the mask. Thus, through the mask inspection operation and the dust particle removal operation mentioned above, a high yield manufacture of a semiconductor device can be achieved.

However, in a case where the dust particles are blown away manually, there may arise problems such as mask damage caused by operation errors and generation of dust caused by the presence of operators. Further, in a case where only an operation for blowing away dust particles is performed, as in the case of a conventional method, before a wafer is exposed through use of the mask dust particle inspection must be performed again in order to check removal of the dust particles from the mask. As mentioned above, the conventional method poses problems such as the necessity of complicated operations.

SUMMARY OF THE INVENTION

The present invention has been conceived to solve the previously-mentioned problems, and a general object of the present invention is to provide a novel and useful mask inspection system and a method of manufacturing a semiconductor.

A more specific object of the present invention is to provide a mask inspection system which eliminates repetition of dust particle inspection by simultaneously removing dust particles and checking the removal thereof.

The above objects of the present invention are achieved by a mask inspection system which detects and removes dust particles on a mask. The system includes a gas blowing device blowing gas toward the mask; a dust particle suction device facing the mask; and a particle counter for counting the number of dust particles sucked by the dust particle suction device.

Another object of the present invention is to provide a method of manufacturing a semiconductor device which eliminates the necessity of repetition of dust particle inspection by simultaneously removing dust particles and checking the removal thereof.

The above object of the present invention is achieved by a method of manufacturing a semiconductor device. The method includes the steps of: detecting dust particles on a mask; blowing away the dust particles from the mask by blowing gas while checking whether or not the dust particles are blown away; and exposing a semiconductor wafer through use of the mask for which removal of the dust particles is checked in the dust particle removal checking step.

Other objects and further features of the present invention will be apparent from the following detailed description when read in conjunction with the accompanying drawings.

DESCRIPTION OF THE PREFERRED EMBODIMENTS

Figure 1:
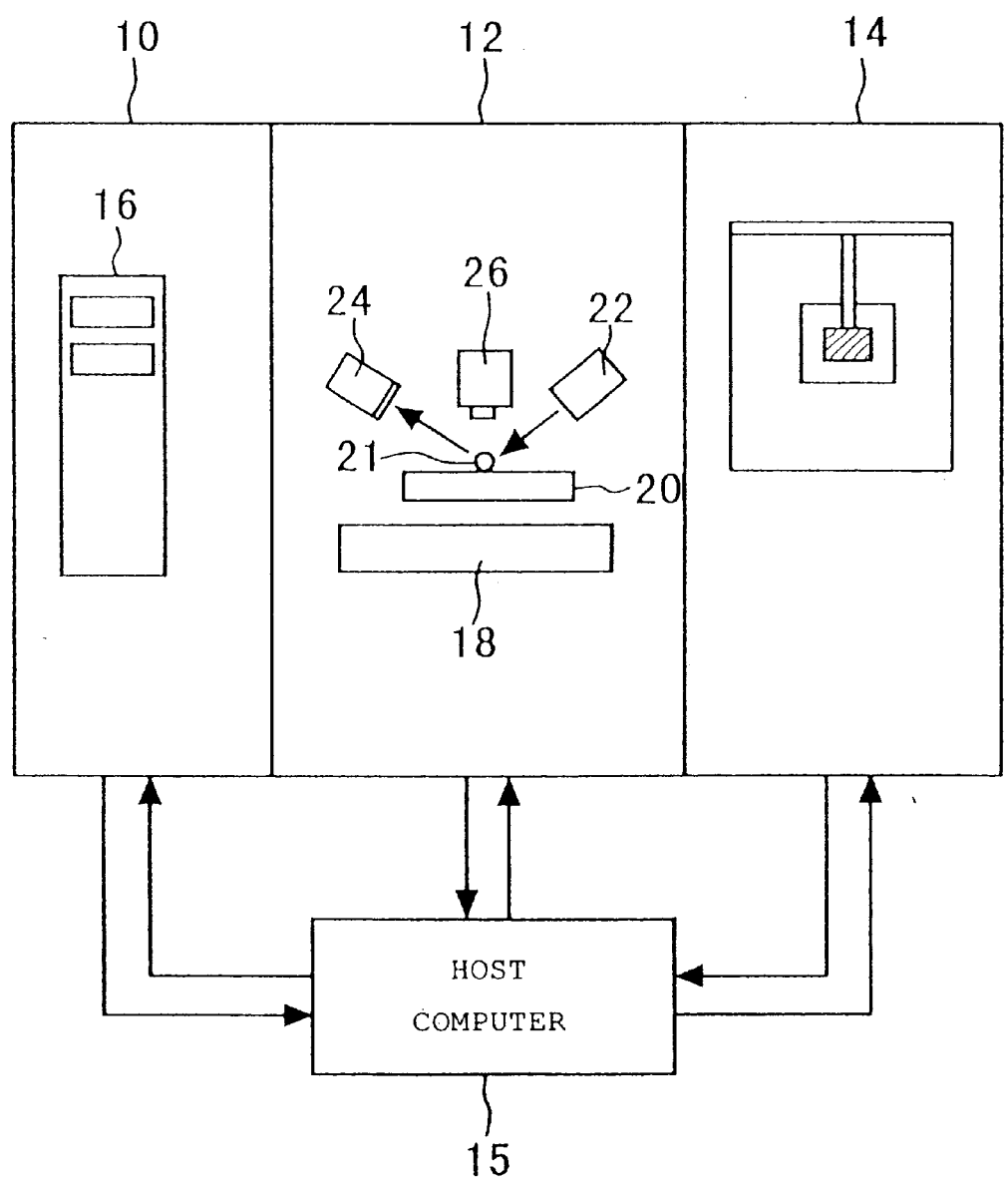
FIG. 1 is a schematic view of a mask inspection system practiced as a first embodiment of a first embodiment of the present invention.

In the following, principles and embodiments of the present invention will be described with reference to the accompanying drawings. Elements common to the drawings will be assigned the same reference numerals, and repetition of their explanations will be omitted.

First Embodiment

FIG. 1 is a schematic view of a mask inspection system practiced as a first embodiment of the present invention. As shown in FIG. 1, the mask inspection system comprises a loader chamber 10, an inspection chamber 12, and a dust removal chamber 14. The loader chamber 10, the inspection chamber 12, and the dust particle removal chamber 14 are capable of communication with a host computer 15. In the first embodiment, the mask inspection system is controlled by the host computer 15.

A mask loader 16 is provided in the loader chamber 10, and masks housed in a case are set in the mask loader 16. The mask loader 16 automatically carries the mask set in thereof to the inspection chamber 12 after activation of the mask inspection system.

An inspection table 18 is provided in the inspection chamber 12. A mask 20 to be checked is set on the inspection table 18. Above the inspection table 18 there are disposed a laser light source 22, a detector 24, and a microscope unit 26. The devices can be displaced relative to the inspection table 18.

The laser light source 22 irradiates a laser beam to the mask 20 set on the inspection table 22 at a given incident angle. The detector 24 detects dust particles 21 on the mask 20 upon detection of scattered light of the laser beam. The mask inspection system according to the first embodiment stores information about the dust particles 21, i.e., the positional coordinates and sizes of the dust particles if the detector 24 detects the dust particles 21 on the mask 20. The microscope unit 26 indicate a magnified image of the thus-detected dust particles for a system operator.

In a case where the dust particles 21 to be removed are detected on the mask 20 in the inspection chamber 12, the mask 20 is carried to the dust particle removal chamber 14 by means of a carrying mechanism. The dust particle removal chamber 14 is the principal section of the mask inspection system practiced as the first embodiment. Now, the structure will be described of the dust particle removal chamber 14 by reference to FIGS. 2 and 3.

Figure 2:
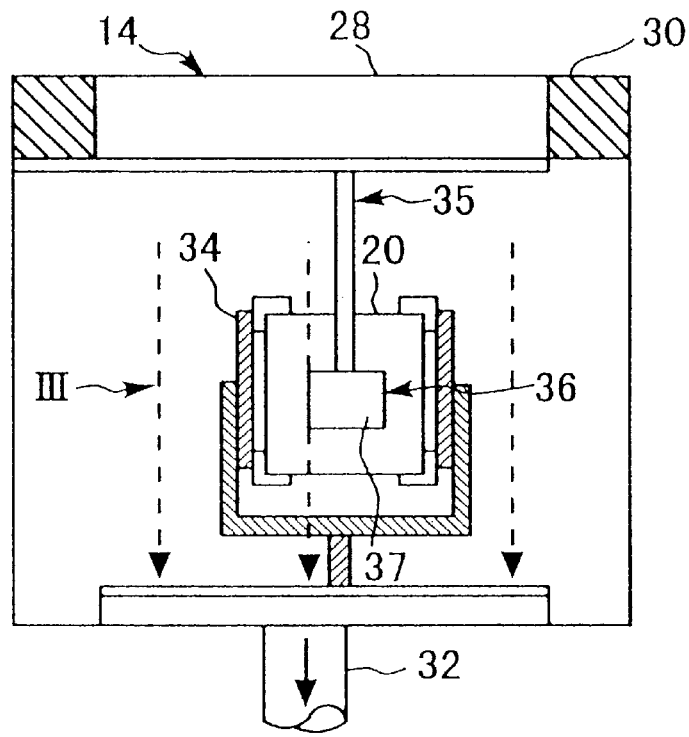
FIG. 2 is an enlarged view of a dust particle removal chamber shown in FIG. 1.

FIG. 2 is an enlarged view of the dust particle removal chamber 14. As shown in FIG. 2, the dust particle removal chamber 14 has a clean unit 28 in an upper portion thereof. The clean unit 28 comprises an ULPA filter and a fan unit. An ionizer 30 is disposed in a side portion of the clean unit 28. The ionizer 30 eliminates the static electricity of dust particles passing through the clean unit 28 in order to prevent the particles from adhering onto the mask 20.

An exhaust pipe 32 is provided in the bottom of the dust particle removal chamber 14. The cleaning unit 28 supplies purified air to the inside of the chamber 14. The air supplied to the chamber 14 is exhausted from the exhaust pipe 32. As a result, airflow streaming from top to bottom as denoted in FIG. 2 by dotted lines is produced in the dust particle removal chamber 14.

A holder 34 is provided in the dust particle removal chamber 14. As shown in FIG. 2, the mask 20 carried from the inspection chamber 12 is held in an upright position in the chamber 14 by means of the holder 34. A position changeable mechanism 35 is also provided in the chamber 14. The position changeable mechanism 35 is fixed to a dust particle removal mechanism 36 at a base section 37 thereof. The position changeable mechanism 35 is capable of actuating the dust particle removal mechanism 36 three-dimensionally. More specifically, the mechanism 35 is capable of actuating the dust particle removal mechanism 36 two-dimensionally within a plane parallel to the mask 20 and in a direction perpendicular to the mask 20.

Figure 3:
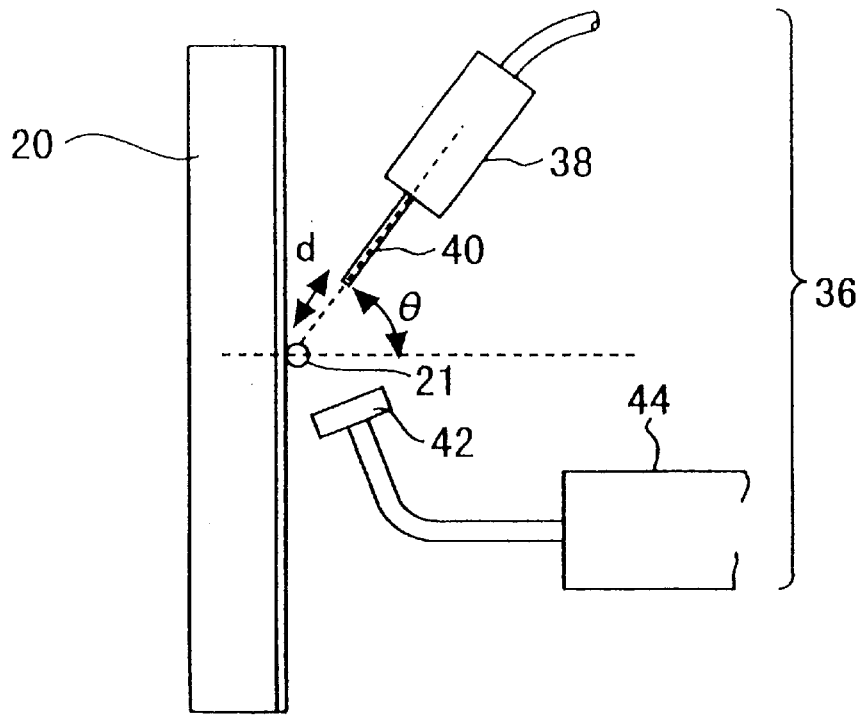
FIG. 3 is a side view of a dust particle removal mechanism and a mask shown in FIG. 2.

FIG. 3 shows a side view of the dust particle removal mechanism 36 and the mask 20 when viewed in direction III in FIG. 2. As shown in FIG. 3, a nozzle 40 is provided at the tip end of the mechanism 36. The nozzle 40 is fixed to a gas blowing device 38 which squirts high-pressure gas so as to remove the dust particles 21 adhering to the mask 20. In order to prevent dust particles from staying in the nozzle 40, purified gas is constantly blown from the nozzle 40.

The gas blowing device 38 is connected to the base section 37 of the dust particle removal mechanism 36. In the first embodiment, the base section 37 is configured in such a way where the distance "d" between the nozzle 40 and the mask 20 and an angle "θ" of the nozzle 40 relative to the mask are allowed to be set arbitrarily. The gas blowing device 38 is configured so as to be able to change the pressure at which gas is blown. In the first embodiment, gas which is unreactive with the material of the mask such as glass, chrome, or MoSiON, more specifically, dry air or nitrogen, is blown from the gas blowing device 38.

The dust particle removal mechanism 36 has a dust particle suction device 42 and a particle counter 44. The dust particle suction device 42 sucks the dust particle 21 removed from the surface of the mask 20. The device 42 is configured in such a way that a suction port thereof is positioned below the tip end of the nozzle 40. The dust particles sucked by the suction device 42 are carried to the particle counter 44, where the number of the dust particles is counted. With the foregoing configuration, it can be determined that one dust particle is removed from the mask 20 when the number of dust particles is incremented by the particle counter 44.

By reference to FIG. 4, there will now be described a series of proceedings to be performed when the mask 20 is checked through use of the mask inspection system practiced as the first embodiment.

Figure 4:
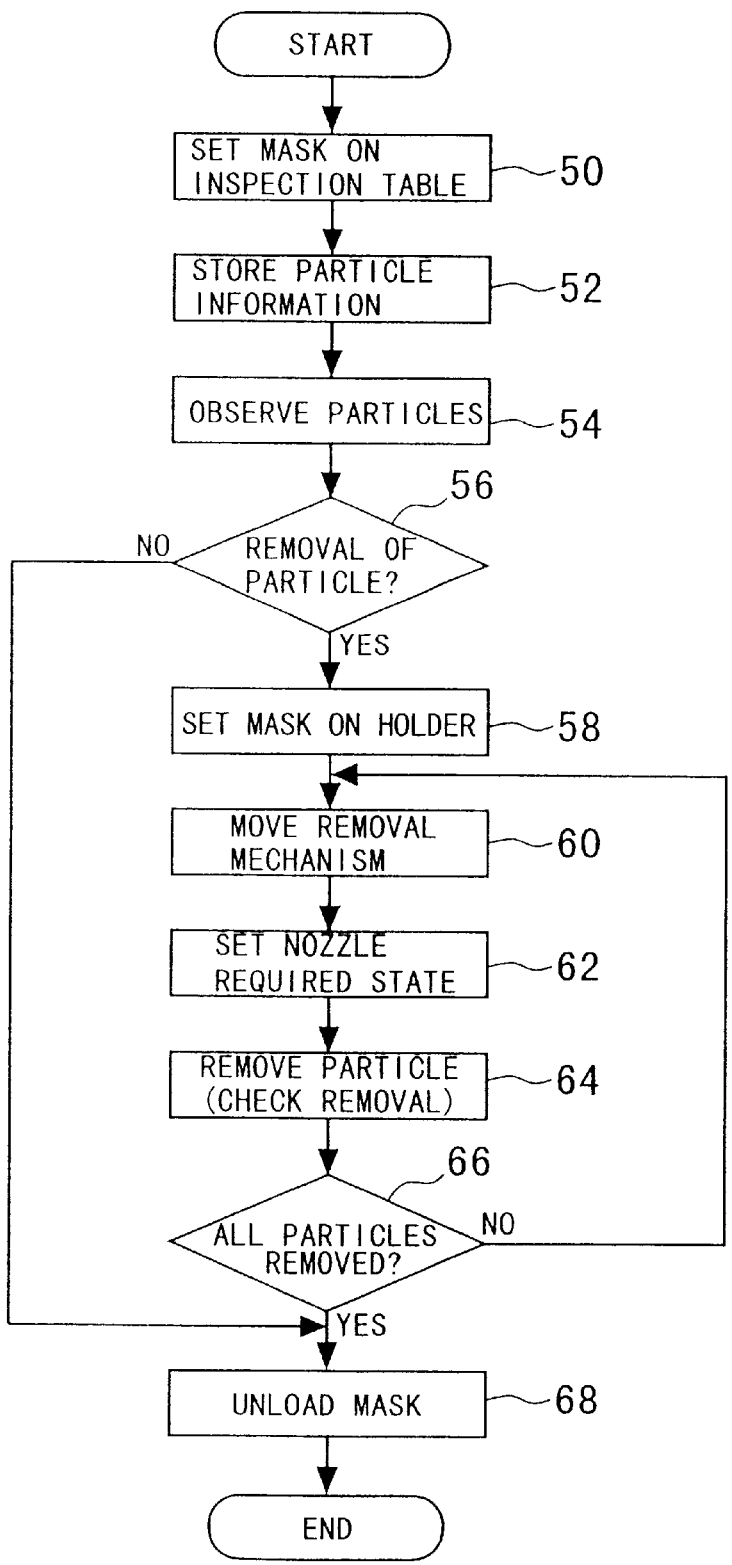
FIG. 4 is a flowchart showing a series of proceedings performed in a mask inspection process in which the mask inspection system shown in FIG. 1 is used.

FIG. 4 is a flowchart showing a series of proceedings performed during the process of inspection of the mask 20. The proceedings shown in FIG. 4 are performed after a start switch of the mask inspection system is turned on. In the proceedings shown in FIG. 4, the processing in step 50 is carried out first.

In step 50, the mask 20 housed in the mask loader is carried to the inspection chamber 12 and set on the inspection table 20.

In step 52, a check is made as to whether or not dust particles are present on the surface of the mask 20. During the processing, the entire surface of the mask 20 is automatically scanned by means of the laser light source 22 and the detector 24. The mask inspection system stores information about all the dust particles on the mask 20, such as the positional coordinates and sizes of dust particles during the scanning operations.

In step 54, dust particles are observed. All the detected dust particles are sequentially indicated for the system operator by means of the microscope 26 after completion of the processing in step 52. The system operator is required to observe the detected dust particles through visual check of the displayed image in this step.

In step 56, it is determined by the system operator whether or not removal of dust particles is necessary based on an observation result. If the operator decides that there is no necessity of removing the dust particles, processing in step 68 is performed. In contrast, if the operator decides that dust particles must be removed, processing in step 58 is performed.

In step 58, the mask 20 to be checked is carried to the dust particle removal chamber 14 from the inspection chamber 12, and set on the holder 34. As mentioned above, the air inside the dust particle removal chamber 14 flows in the direction from top to bottom. Accordingly, the dust particles suspended in the air within the chamber 14 fall in the direction from top to bottom under the influence of gravity and airflow. As mentioned above, the mask 20 is supported in an upright position in the dust particle removal chamber 14 by means of the holder 34. In this case, since the dust particles move in the direction parallel to the mask 20, the suspended dust particles can be effectively prevented from newly adhering to the mask 20.

In step 60, the dust particle removal mechanism 36 is moved to suitable positions based on the positional coordinates of the dust particles 21 to be removed.

In step 62, the nozzle 40 is set to a required state on the basis of the sizes and shapes of the dust particles 21. The mask inspection system stores the relationship between the size and shape of each dust particle and the conditions suitable for removing the dust particle (conditions such as the distance "d" and angle "θ" of the nozzle 40 and the pressure at which gas is blown). In step 62, the conditions corresponding to the dust particles 21 to be removed are selected on the basis of the stored data, and the distance "d," the angle "θ," and the blowing pressure are set to the values satisfying the conditions.

In step 64, removal of dust particles and checking of removal of the dust particles are performed. After the nozzle 40 setting in step 62, high-pressure gas is effectively blown toward the dust particles 21. As a result, the dust particles 21 are immediately removed from the surface of the mask 20 after completion of the processing in step 62. As mentioned above, in the first embodiment, the dust particle suction device 42 is disposed such that the suction port of the suction device is situated at a position below the tip end of the nozzle 40. Because of this positional relationship, the dust particles 21 blown away by the gas blown from the nozzle 40 are captured by the dust particle suction device 42 with a high probability.

When the dust particles 21 are captured by the dust particle suction device 42, they are carried to the particle counter 44, where the number of dust particles 21 is counted. The number of dust particles 21 is incremented only when the dust particles 21 are removed from the surface of the mask 20. Accordingly, the mask inspection system enables checking of removal of the dust particles 21 through counting operations. The processing in step 64 is completed after the removal of dust particles 21 has been checked by means of the aforementioned technique.

As mentioned above, the mask inspection system removes the dust particles 21 and checks the removal of the dust particles 21 simultaneously. For this reason, the mask inspection system eliminates the necessity of performing checking operations for checking removal of dust particles 21 after removal of the same. Accordingly, through use of the mask inspection system according to the first embodiment, system throughput in the mask checking process can be improved.

In step 66, it is determined whether or not all the dust particles detected on the mask 20 have been removed. If all the particles are determined to have already been removed, processing in step 68 is performed. In contrast, if all the particles are determined to have not yet been removed, the processing operations in step 60 through 66 are performed with regard to the dust particles still remaining on the mask 20.

In step 68, the mask 20 set in the dust particle removal chamber 14 or the inspection chamber 12 is unloaded to the loader chamber 10. After unloading of the mask, the series of processing operations shown in FIG. 4 is now completed. As mentioned above, the mask inspection system according to the first embodiment enables automatic execution of all the processing steps related to inspection and removal of dust particles. Therefore, contamination of a mask can be reliably checked through use of the mask inspection system, without involving mask damage or generation of dust particles, which would otherwise be caused by the presence of an operator.

Although in the first embodiment the description has explained the case where a pellicle is not provided on the mask 20, the inspection system can be used in a case where a pellicle is provided on a mask. In this case, dust particles on the mask can be removed in the same manner as in the case where a pellicle is not provided on the mask, by optimizing the distance "d" between the surface of the pellicle and the tip end of the nozzle 40.

In the first embodiment, dust particles are removed from only one surface of the mask 20. Dust particles may be removed from both sides of the mask 20 by reversing the mask 20 in the dust particle removal chamber 14 or carrying the dust particle removal mechanism 36 to the reverse side of the mask 20.

Second Embodiment

Figure 5:
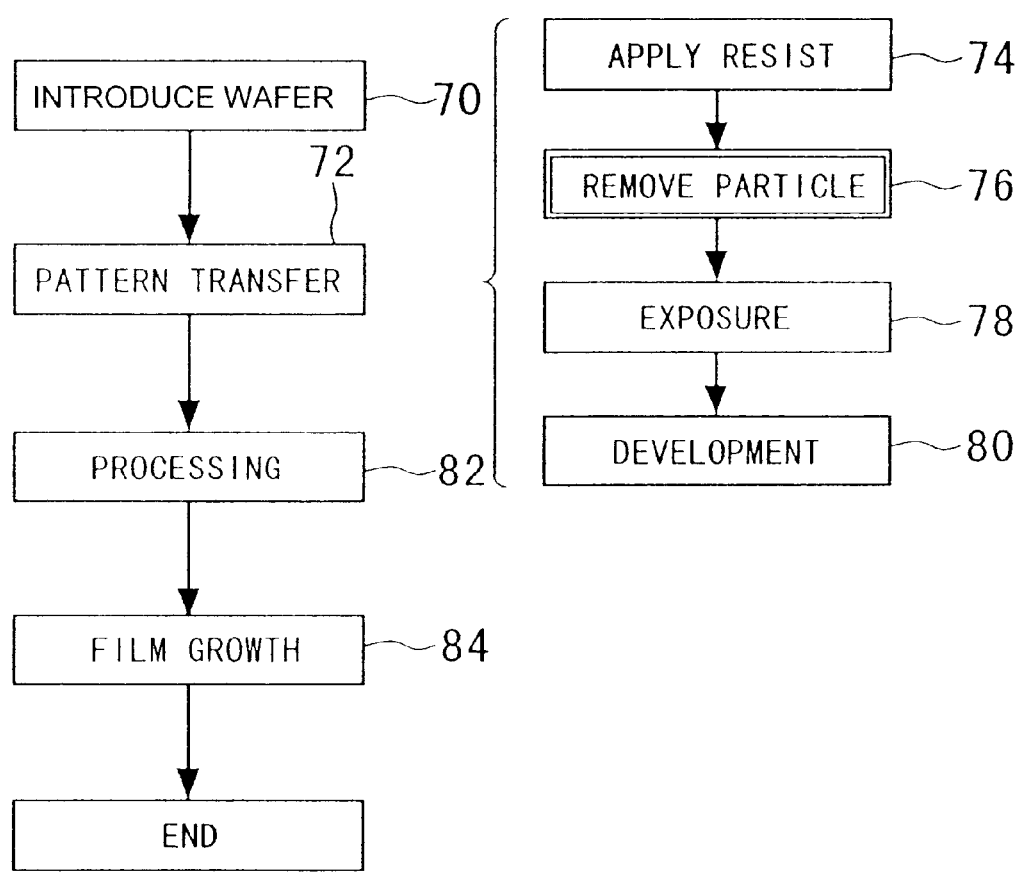
FIG. 5 is flowchart showing a series of proceedings performed in a method of manufacturing a semiconductor device practiced as a second embodiment of the present invention.

A second embodiment of the present embodiment will now be described by reference to FIG. 5. FIG. 5 is a flowchart showing a series of proceedings performed under a method of manufacturing a semiconductor device practiced as the second embodiment.

In the semiconductor device manufacturing method according to the second embodiment, a wafer is introduced into a manufacturing system in step 70. In step 72, a desired pattern is transferred onto the wafer. More specifically, the transfer process (step 72) includes proceedings provided in steps 74 to 80, which will be described below.

In step 74, resist is applied to the wafer. In step 76, dust particles are removed from the transfer-ready mask through use of the mask inspection system according to the first embodiment. The method of manufacturing a semiconductor device practiced as the second embodiment is characterized by the processing in step 76 being incorporated into the transfer process.

In step 78, the wafer is exposed through use of the mask from which dust particles have been removed.

In step 80, the wafer is subjected to a development processing.

After completion of the transfer process in step 72, the series of proceedings shown in FIG. 5 is now completed by execution of processing in step 82 and film growth operations in step 84. As mentioned above, the mask inspection system according to the first embodiment enables immediate, reliable elimination of dust particles from a mask. Accordingly, the manufacturing method including the foregoing proceedings practiced as the second embodiment of the present invention increases the efficiency of production of a semiconductor device as well as improves the reliability of the same.

The present invention having the foregoing configuration yields the following advantageous results.

According to a first aspect of the present invention, dust particles blown away from a mask by a gas blowing device are sucked by means of a dust particle suction device. The dust particles sucked by the dust particle suction device are counted by a particle counter. Accordingly, the present invention enables reliable detection, on the basis of a counted value of the particle counter, as to whether or not dust particles are removed from the mask.

According to a second aspect of the present invention, gas is blown onto dust particles by a gas blowing device from a position above a dust particle suction device, and the suction device sucks the dust particles at a position below the gas blowing device. Dust particles, therefore, can be efficiently guided to the suction device. Accordingly, the present invention enables detection of removal of dust particles with a high probability.

According to a third aspect of the present invention, the relative positional relationship between the gas blowing device and the mask can be changed, and hence various types of dust particles can be efficiently removed from the mask.

According to a fourth aspect of the present invention, the pressure at which gas is blown from the gas blowing device can be changed, and hence various types of dust particles can be efficiently removed from the mask.

According to a fifth aspect of the present invention, since the mask is held in an upright position at the time of removal of dust particles from the mask, the dust particles falling in the direction from top to bottom can be effectively prevented from newly adhering to the mask during the removal of dust particles.

According to a sixth aspect of the present invention, air can flow in the direction from top to bottom within a dust particle removal chamber in which dust particles are removed from the mask. More specifically, air can flow in the direction parallel to the mask. Accordingly, the present invention enables effective prevention of dust particles from newly adhering to the mask within the dust particle removal chamber.

According to a seventh aspect of the present invention, dust particles can be reliably removed from the mask in the process of manufacturing a semiconductor device, prior to exposure of a wafer. Accordingly, the present invention enables high-yield manufacture of a semiconductor device in an easy manner.

Further, the present invention is not limited to these embodiments, but variations and modifications may be made without departing from the scope of the present invention.

What is claimed is:

1. A mask inspection system which detects and removes dust particles on a mask, the system comprising:
   a gas blowing device blowing gas toward the mask;
   a dust particle suction device facing the mask; and
   a particle counter for counting the number of dust particles sucked by the dust particle suction device.

2. The mask inspection system as defined in claim 1, further comprising a pressure variable mechanism which changes the pressure of the gas blown from the gas blowing mechanism.

3. The mask inspection system as defined in claim 1, further comprising a holder which holds the mask in an upright position when the dust particles are removed from the mask by means of the gas blowing device and the dust particle suction device.

4. The mask inspection system as defined in claim 3, further comprising:
   a dust particle removal chamber which stores the mask when the dust particles are removed from the mask by means of the gas blowing device and the dust particle suction device; and
   an airflow mechanism which produces airflow streaming in the direction from top to bottom within the dust particle removal chamber.

5. A method of manufacturing a semiconductor device comprising the steps of:
   detecting dust particles on a mask;
   blowing away the dust particles from the mask by blowing gas while checking whether or not the dust particles are blown away; and
   exposing a semiconductor wafer through use of the mask for which removal of the dust particles is checked in the dust particle removal checking step.

6. A mask inspection system which detects and removes dust particles on a mask, the system comprising:
   a gas blowing device blowing gas toward the mask from a position above a dust particle suction device;
   the dust particle suction device facing the mask, wherein the dust particle suction device sucks dust particles at a position below the gas blowing device; and
   a particle counter for counting the number of dust particles sucked by the dust particle suction device.

7. A mask inspection system which detects and removes dust particles on a mask, the system comprising:
   a gas blowing device blowing gas toward the mask;
   a dust particle suction device facing the mask;
   a particle counter for counting the number of dust particles sucked by the dust particle suction device; and
   a position changeable mechanism which changes a relative positional relationship between the gas blowing device and mask.

* * * * *